United States Patent
Loomas

(10) Patent No.: US 6,514,290 B1
(45) Date of Patent: Feb. 4, 2003

(54) LUNG ELASTIC RECOIL RESTORING OR TISSUE COMPRESSING DEVICE AND METHOD

(75) Inventor: Bryan Loomas, Los Gatos, CA (US)

(73) Assignee: Broncus Technologies, Inc., Mountain View, CA (US)

(*) Notice: Subject to any disclaimer, the term of this patent is extended or adjusted under 35 U.S.C. 154(b) by 0 days.

(21) Appl. No.: 09/680,645

(22) Filed: Oct. 6, 2000

Related U.S. Application Data

(60) Provisional application No. 60/193,940, filed on Mar. 31, 2000.

(51) Int. Cl.[7] ................................................. A61F 2/36
(52) U.S. Cl. ...................... 623/23.65; 600/37; 606/232
(58) Field of Search ................ 623/23.64, 23.65–23.69; 600/37; 606/232

(56) References Cited

U.S. PATENT DOCUMENTS

| | | | |
|---|---|---|---|
| 5,263,982 A | | 11/1993 | Shimomura et al. |
| 5,413,601 A | * | 5/1995 | Keshelava ............... 623/23.65 |
| 5,609,632 A | * | 3/1997 | Elgas ...................... 623/23.65 |
| 5,843,008 A | * | 12/1998 | Gerhard ......................... 602/5 |
| 6,090,996 A | | 7/2000 | Li |
| 6,120,539 A | | 9/2000 | Eldridge et al. |
| 6,123,663 A | * | 9/2000 | Rebuffat ...................... 600/37 |
| 6,153,292 A | | 11/2000 | Bell et al. |
| 6,174,323 B1 | * | 1/2001 | Biggs et al. ................ 606/232 |
| 6,183,593 B1 | | 2/2001 | Narang et al. |
| 6,270,530 B1 | * | 8/2001 | Eldridge et al. .......... 623/23.74 |
| 6,287,290 B1 | | 9/2001 | Perkins et al. |
| 6,293,951 B1 | | 9/2001 | Alferness et al. |
| 6,328,689 B1 | | 12/2001 | Gonzalez et al. |
| 6,416,554 B1 | * | 7/2002 | Alferness et al. ........ 623/23.65 |
| 2001/0037808 A1 | | 11/2001 | Deem et al. |

FOREIGN PATENT DOCUMENTS

| | | | |
|---|---|---|---|
| EP | 1078601 A2 | * 2/2001 | ............. 623/23.65 |
| EP | 1 078 601 A2 | 2/2001 | |
| WO | WO 98/01084 A1 | 1/1998 | |
| WO | WO 98/14136 A1 | 4/1998 | |
| WO | WO 98/48706 A1 | 11/1998 | |
| WO | WO 00/02500 A1 | 1/2000 | |
| WO | WO 01/02042 A1 | 1/2001 | |
| WO | WO 01/13839 A1 | 3/2001 | |
| WO | WO 01/13908 A2 | 3/2001 | |

OTHER PUBLICATIONS

Netter, F. H. (1992). "Respiratory System," vol. 7 *In The CIBA Collection of Medical Illustrations*, Divertie, M.B. et al. eds., CIBA–GEIGY Corporation: New Jersey, p. 267.

* cited by examiner

*Primary Examiner*—David H. Willse
*Assistant Examiner*—Suzette J. Jackson
(74) *Attorney, Agent, or Firm*—Morrison & Foerster LLP

(57) ABSTRACT

This relates to restoring recoil or maintaining compression of an emphysematous or otherwise unhealthy lung and includes elastic members which contract or compress the lung tissue. The elastic member is secured to tissue of the lung either inside or outside of the lung to supplement the natural elasticity of the lung or maintain the tissue in a compressed state. The elastic member may include elastic patches, elastic bands, coil springs, covers or a combination of these elements.

13 Claims, 4 Drawing Sheets

LUNG ELASTIC RECOIL RESTORING OR TISSUE COMPRESSING DEVICE AND METHOD

This application claims benefit of application Ser. No. 60/193,940 filed Mar. 31, 2000.

BACKGROUND OF THE INVENTION

1. Field of the Invention

The invention relates to a device and method for restoring lung function, and more particularly, the invention relates to a device and method for restoring the elasticity or recoil of a lung to improve pulmonary function by increasing gas exchange or for restoring the efficiency of the lung by compressing the less useful, diseased portions of the lungs.

2. Brief Description of the Related Art

Chronic obstructive pulmonary diseases (COPD), such as emphysema are steadily increasing in frequency, possibly due to continued smoking, increasing air pollution, and the continued aging of the population. Emphysema patients have reduced lung capacity and efficiency due to the breakdown of lung tissue often caused by smoking. Healthy lung tissue includes a multitude of air passageways leading to tiny air sacks called alveoli throughout the lung which inflate and deflate with air when we breath. The alveoli are small, tightly packed, polyhedral recesses composed of a fibrillated connective tissue and surrounded by a few involuntary muscular and elastic fibers. The thin walls of the alveoli perform gas exchange as we inhale and exhale. The lungs are expanded to draw air into the alveoli by moving the diaphragm downward and moving the chest outward. The air is expelled from the lungs by the natural elasticity or recoil of the lung tissue in combination with the pushing of the diaphragm back up into place by the abdominal contents.

In the lungs of an emphysema patient, the walls between adjacent alveoli within the alveolar sac deteriorate. This wall deterioration is accelerated by the chemicals in smoke which affect the production of mucus in the lungs. Although the breakdown of the walls of the alveoli in the lungs occurs over time even in a healthy patient, this deterioration is greatly accelerated in a smoker causing the smoker's lungs to have multiple large spaces with few connecting walls instead of the much smaller and more dense alveoli spaces in healthy lung tissue.

In a diseased emphysematous lung many of the walls of alveoli and other lung tissue are deteriorated. Because of the deterioration, the diseased lung has larger open spaces and a larger overall volume than a healthy lung. However, the diseased lung is less efficient as it has less wall tissue to achieve gas exchange.

In addition, deterioration of the lung tissue in an emphysematous lung reduces the amount of elastic fibers within the lung and thus reduces the overall elasticity of the lung. The reduction of the lung's elasticity permits the chest wall to pull the lung outward more easily and reduces the lung's ability to contract or recoil to expel air. This inability of the lung tissue to recoil results in a larger residual volume of air remaining in the lungs after exhalation. Consequently, this increased residual gas volume interferes with the ability of the lung to draw in additional gas during inspiration. As a result, a person with advanced COPD can only take short shallow breaths. Accordingly, emphysema patients often have a flattened diaphragm, a barrel chest or enlarged chest, and shoulders which are shrugged upwards. When patients with severe emphysema take in as much air as their chest cavity can accommodate, they still have insufficient gas exchange because their chest is full of non-functional air filling the large cavities in the lungs. This non-functional residual air cannot be expelled from the lungs. As a result, this decreased lung efficiency causes even the most ordinary activities to be extremely difficult causing the patient to lose mobility.

In cases of severe emphysema, lung volume reduction surgery (LVRS) attempts to improve lung efficiency to allow the patient to regain mobility. In lung volume reduction surgery, a diseased portion of an emphysematous lung having alveolar wall deterioration is surgically removed. LVRS is performed by opening the chest cavity, retracting the ribs, stapling off, and removing the more diseased portion of the lung. The removal of the diseased lung tissue allows the remaining healthier tissue to inflate more fully and take greater advantage of the body's ability to inhale and exhale. Since there is more air and more gas exchange in the healthier portion of the lung, lung efficiency improves.

LVRS addresses the loss in lung efficiency but does not address the loss of the natural lung tissue elasticity in a diseased lung. In addition, LVRS is an extremely invasive procedure having substantial risks of serious post-operative complications, such as pneumothorax, and requires an extended convalescence.

Accordingly, it is desirable to achieve improved lung efficiency for emphysema patients by improving lung elasticity or recoil, or by providing a means to reduce the volume of the diseased portions of the lung through tissue compression.

SUMMARY OF THE INVENTION

The present invention relates to a device and method to improve lung efficiency by restoring recoil of an emphysematous or otherwise unhealthy lung. The present invention may also improve lung efficiency by reducing the volume of diseased portions of the lung through compression of lung. Compressing certain portions of lung tissue prevents expansion and over-inflation of this lung tissue which increases the volume within the chest cavity and allows otherwise increased expansion of relatively healthier lung tissue. A device for either restoring recoil or mechanically compressing lung tissue may include at least one elastic member positioned inside or outside of the lung and which is secured to the lung tissue and supplements the natural elasticity of the lung or compresses that portion of lung.

In accordance with one variation of the present invention, a device for restoring lung recoil ability may include a bio-compatible elastic member having at least a first end and a second end, the elastic member having sufficient elasticity which is capable of compressing lung tissue when applied to a lung. The elastic member may also be capable of being stretched by the lung tissue during inhalation. The first end and the second end of the elastic member may be fixed to the lung tissue with the elastic member in a stretched condition to improve the elasticity of a lung.

The variations describe above may also be configured to have an elasticity which, when placed over a compressed lung or a compressed portion of the lung, prevents expansion of the lung tissue during inspiration. Alternatively, the present invention includes a covering which prevents the lung or portions of the lung from significantly expanding in volume during inspiration. These variations may also be configured to mechanically compress the diseased lung tissue as well.

BRIEF DESCRIPTION OF THE DRAWING

The invention will now be described in greater detail with reference to the preferred embodiments illustrated in the accompanying drawings, in which like elements bear like reference numerals, and wherein.

DETAILED DESCRIPTION

The present invention includes a method and device to relieve the effects of emphysema and other lung disease by increasing the efficiency of gas exchange in the lung. This is achieved by securing elastic members to the lung tissue to increase the elasticity and recoil of the lung tissue. The elastic member may also mechanically compress diseased portions of the lung. The elastic members may be secured around an exterior of the lung or secured to tissue inside the lung.

An emphysematous lung generally includes areas of tissue deterioration which cause a cross section of lung tissue to appear similar to a cross section of Swiss cheese. When tissue deterioration occurs pulmonary function is impaired to a great degree by the lack of tissue available to provide the gas exchange function and the reduction in the natural elasticity of the lung due to the loss of tissue.

The following illustrations are examples of the invention described herein. It is contemplated that combinations of aspects of specific embodiments or combinations of the specific embodiments themselves are within the scope of this disclosure.

Figure 1:
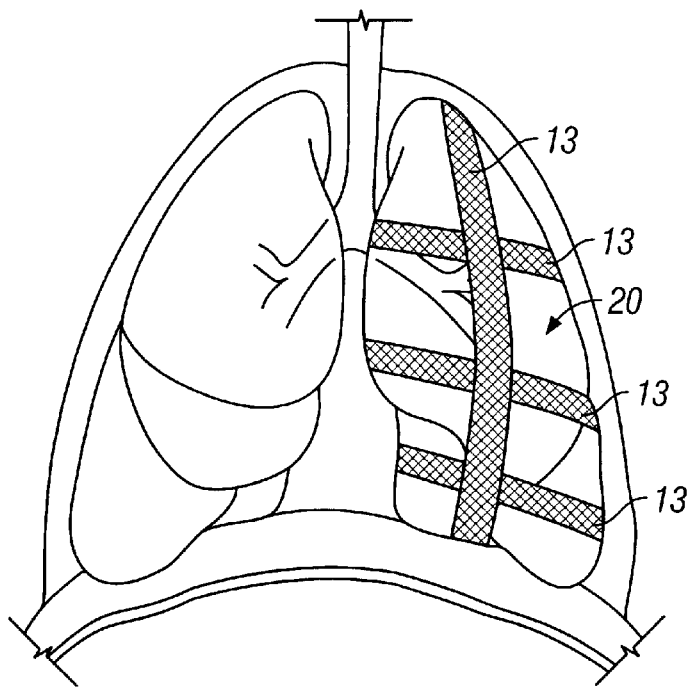
FIG. 1 is a front view of a lung cavity having a lung treated with elastic bands according to the present invention.

A variation of the invention illustrated in FIG. 1 includes a plurality of elastic bands 13 positioned around a lung 20 to restore the elasticity of the lung. The elastic bands 13 may be formed of a bio-compatible elastic material. The elastic material may be formed into strips that can be secured around the lung. The elastic bands 13 may have an elasticity which is sufficient to compress the lung tissue, yet, the elastic band should be capable of being stretched by the lung tissue during inhalation. The elasticity of the elastic bands 13 may also be selected such that the bands only serve to compress portions of the lung. One variation of the invention includes elastic bands 13 that are secured to an exterior of the lung 20 at one or more spaced positions along their lengths. The bands may be anchored to the lung tissue. It is contemplated that the term anchors or anchored includes the use of any bio-compatible adhesive, permanent or temporary suture, mechanical device, agent which permits attachment of a band to the tissue via fibrosis of lung tissue, or any other apparatus which affixes to the lung tissue or affixes to another band so that the affixed bands are secured to the lung tissue. Another example of anchoring devices which may be used in the present invention is found in U.S. Pat. application Ser. No. 09/576,786 entitled "METHOD AND ASSEMBLY FOR LUNG VOLUME REDUCTION," the entirety of which is incorporated by reference herein. Alternatively, the elastic bands 13 may be held in place by a friction fit.

As shown in FIG. 1, the lung 20 may be treated by placing one substantially vertical elastic band 13 and three substantially horizontally spaced apart elastic bands around the lung. It is contemplated that any number of bands may be used as needed. Moreover, the arrangement of the elastic bands 13 illustrated in FIG. 1 is merely exemplary. Preferably, the elastic bands 13 are placed in a crossing or interlocking pattern covering substantially the entire lung 20. Application of the elastic bands 13 around the lung may be performed surgically by opening the chest cavity and placing the bands on the lung or may be performed minimally invasively through small incisions made between the ribs of the patient. The number, elasticity, and positioning of the bands 13 around the lung 20 may be designed to restore the dynamic balance of the lung to prevent over inflation. of the lung and restore the lung's normal range of motion. In the variation where the elasticity of the bands 13 is such that the band compresses lung tissue and prevents the tissue from expanding during inhalation, the band functions to increase the volume within the chest cavity so that healthier lung tissue has more volume to expand and function in oxygen exchange. The elastic bands 13 may be used on one lung or on both lungs depending on the condition of the patient.

The elastic bands 13 may be formed of any bio-compatible resilient material, such as silicone or urethane.

Figure 2:
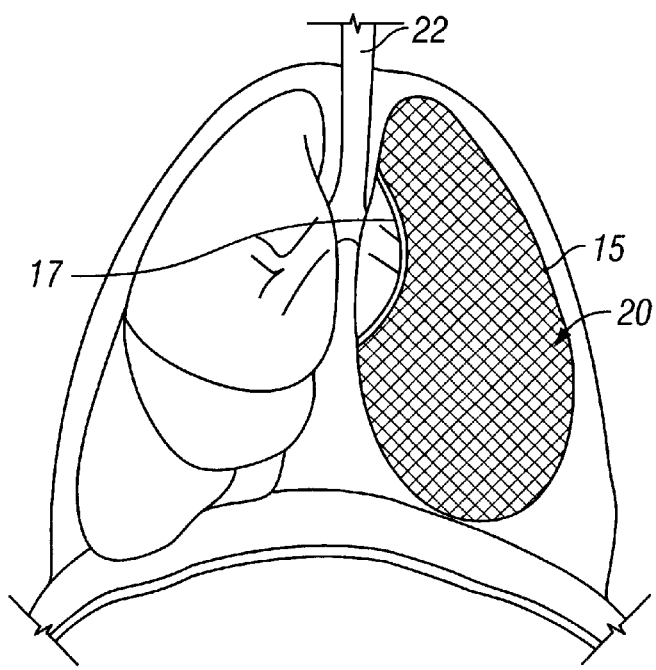
FIG. 2 is a front view of a chest cavity having a lung treated with an elastic bag according to the present invention.

FIG. 2 illustrates an alternative variation of the invention in which an elastic bag 15 is secured around the lung 20 to restore the elastic recoil of the lung. The elastic bag 15 may be formed of a bio-compatible resilient material which may be shaped substantially in the shape of the lung. The elastic bag 15 may have an elastic neck 17 which accommodates the bronchus 22 without causing a constriction of the bronchus. As in the embodiment of FIG. 1, the elastic bag 15 can be placed over the lung by surgically opening the chest or minimally invasively through small access ports between the ribs. The elastic bag 15 may be formed of any bio-compatible elastic material, such as silicone or urethane.

Figure 3:
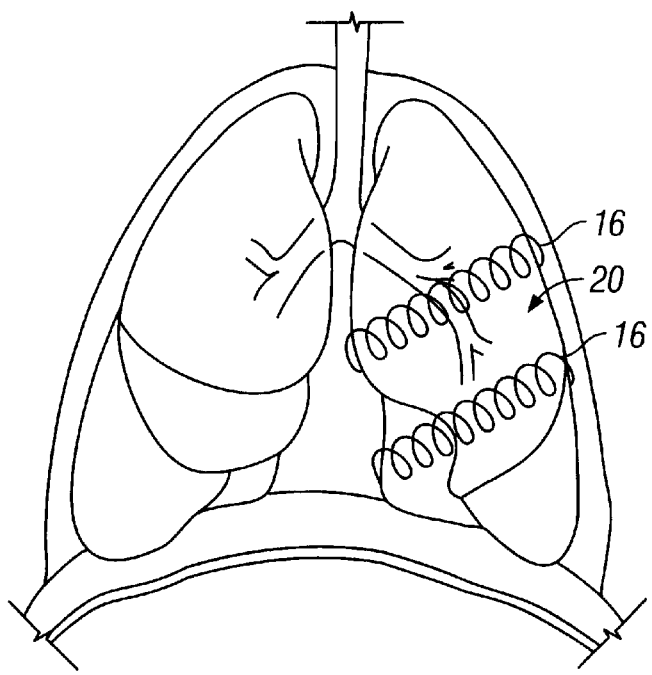
FIG. 3 is a front view of a chest cavity having a lung treated by elastic spring elements according to the present invention.

FIG. 3 illustrates a further embodiment of the invention in which elastic spring elements 16 are secured to or wrapped around the lung 20 to restore lung recoil ability. The spring elements 16 may be continuous loop members fitted around the lung 20 or may be segments secured on either end to the lung tissue by tissue anchors as mentioned above. The spring elements 16 may be formed of bio-compatible materials, such as stainless steel, MP35N, or either of these materials coated or interwoven with silicone or urethane.

Figure 4:
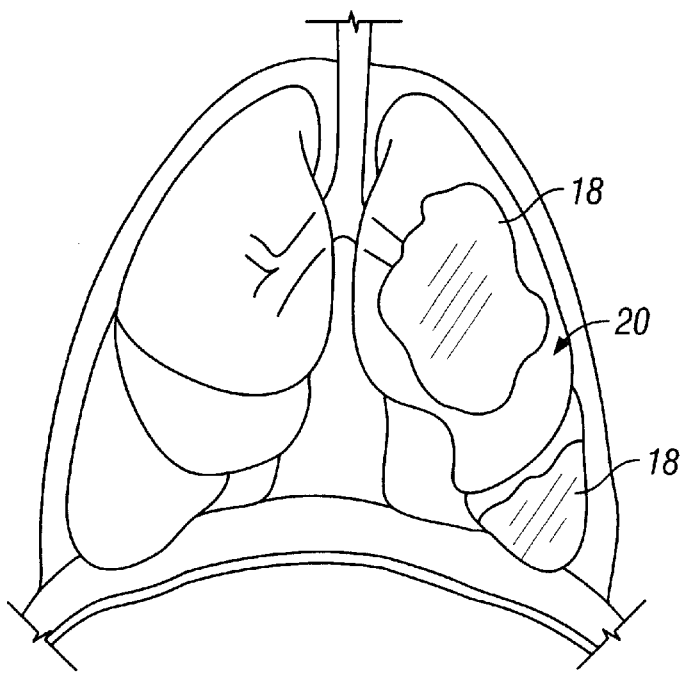
FIG. 4 is a front view of a chest cavity having a lung treated by elastic patches according to the present invention.

Another variation of the invention, shown in FIG. 4, may include one or more elastic patches 18 adhered to the exterior surface of the lung 20. The elastic patches 18 may adhere to an exterior of the lung by an adhesive or other mechanism and function to restore the lung recoil ability. The elastic patches 18 can be sized and shaped to target a particular diseased region of the lung 20 for restoring lung recoil ability of that particular region. Also, the elastic patches 18 may be relatively in-elastic when compared to the lung tissue. In such a case, the elastic patches. 18 compress the lung tissue and prevent the lung tissue from expanding during inhalation, thereby increasing the volume within the chest cavity into which healthier lung tissue may expand. The patches 18 may be applied as sheets or may be applied as a liquid or a paste which cures after application and bonds to the lung tissue. Examples of bio-compatible elastic patch materials include silicon, urethane, etc.

Figure 5:
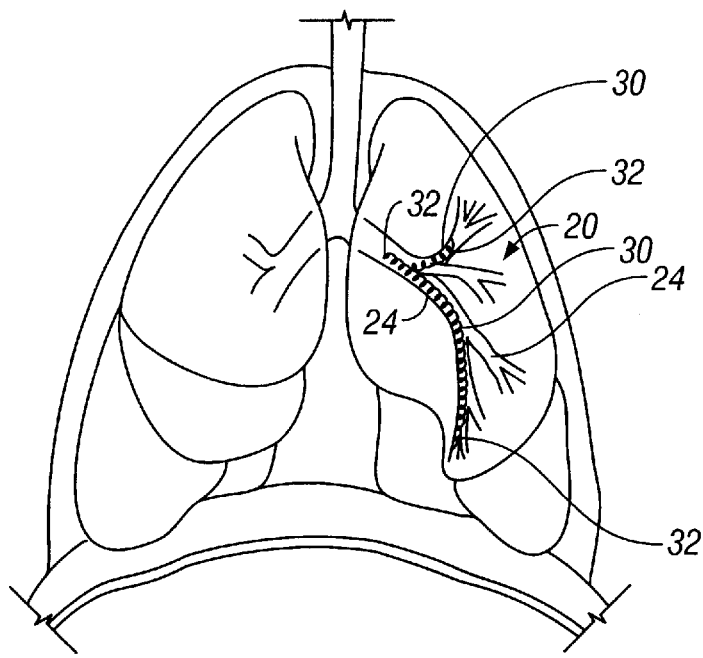
FIG. 5 is a front view of a chest cavity with a lung shown in cross section which has been treated by internal elastic elements according to the present invention.

FIG. 5 illustrates a further alternative variation of the invention for restoring lung recoil ability from an inside of the lung 20. The device of FIG. 5 may include one or more elastic members 30 such as elastic spring elements or elastic bands. The elastic members 30 may be inserted into one or more air passageway 24 in the lungs, stretched, and secured at their ends 32 to the interior of the lung. The elastic members 30 extend through the air passageways 24 of the lung without blocking the air passing though the air passageways. The anchors 32 may be mechanical fastening mechanisms which secure the ends of the elastic members 30 to the lung tissue. Anchors 32 may also be provided to secure portions of the elastic members 30 between the ends. The anchors 32 may include one or more hooks, barbs, and the like which securely engage the tissue of the interior of the air passageways 24. Although the invention has been illustrated with the anchors 32 secured within the air passageways, it is also possible that the anchors could be secured by rigid or semi-rigid members that extend through the airway wall into the parenchyma or lung tissue to ensure that the anchors do not pull loose. The device of FIG. 5 may be implemented by inserting the elastic members 30 and anchors 32 into place in the interior of the lung through the bronchus of the patient using a bronchoscope and associated tools. The elastic members 30 may be formed of a bio-compatible material, such as silicone, urethane, stainless steel, or MP35N, or a combination thereof.

Figure 6A:
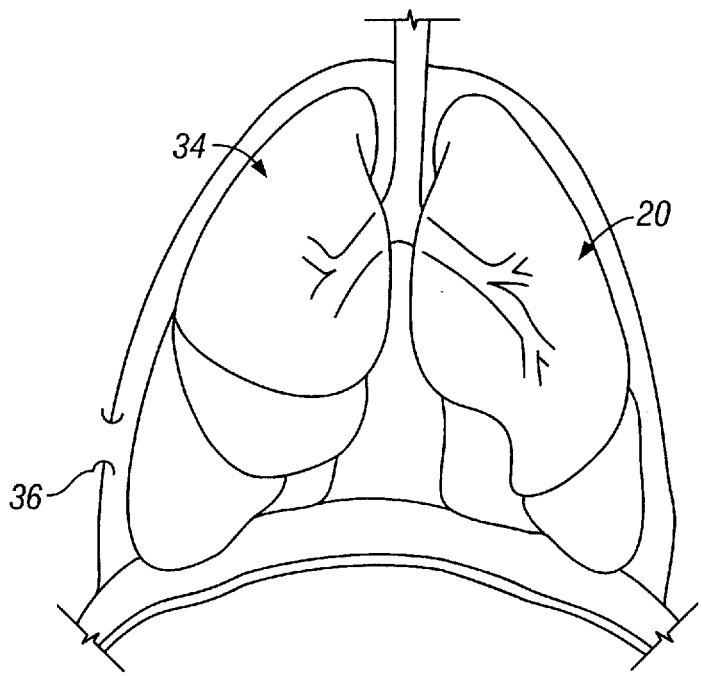
FIGS. 6A–6C illustrate the lungs beforehand after one lung is reduced in volume to free space within the chest cavity for the other lung to expand.
Figure 6B:
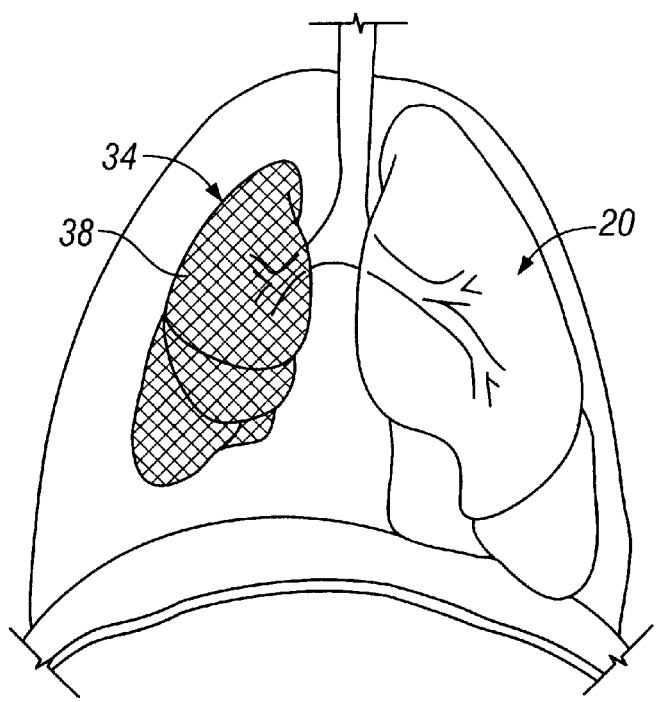
Figure 6C:
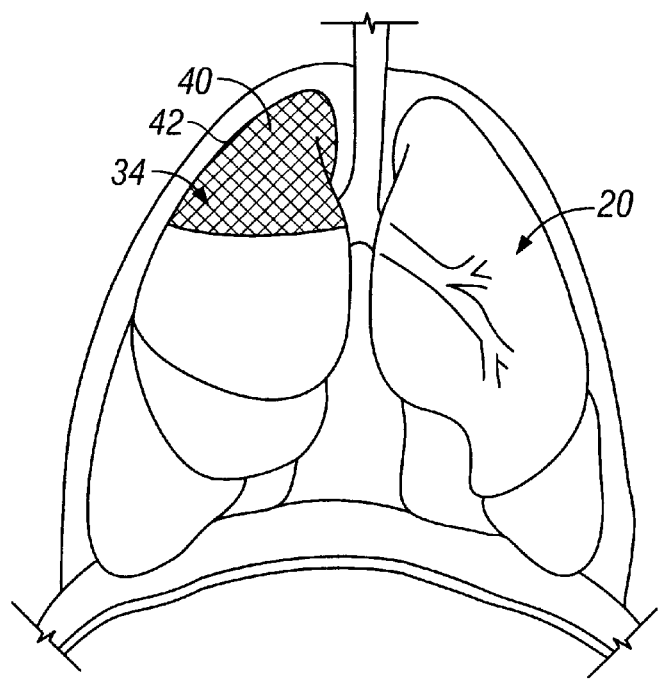

FIGS. 6A–6C illustrates yet another variation of the invention. In attaching devices to the lung which either restricting the expansion of the lung or aiding in the elastic recoil of the lung, it may be desirable to compress the lung, or a portion thereof, prior to placement of the device. For example, compression of the lung may be achieved using a mechanical apparatus which forces compression of the lung. Alternatively, increasing the pressure within the chest cavity may also induce compression of the lung. Increasing the pressure within the chest cavity may be accomplished by injecting fluid, gas, etc. within the cavity which raises the pressure in the cavity to sufficiently compress the lung. Another means of raising chest cavity pressure includes venting the chest cavity to atmospheric pressure.

FIG. 6A illustrates an example of raising the chest cavity pressure by venting the chest cavity using a port 36. The port 36 may include a tube, catheter, or other opening in the chest wall which places the chest cavity in fluid communication with atmospheric pressure. If the lung contains a positive pressure ventilation apparatus, removing the apparatus will allow the lung to compress on its own. One of the lungs 20 may remain on a positive pressure ventilation apparatus so that it does not compress with the other lung. Next, as illustrated in FIGS. 6B–6C, a covering 38, 40 is placed on the lung. Although FIGS. 6B–6C illustrate a covering, the device may be any of the devices described herein. After the pressure within the chest cavity is returned to normal, the covering 38 may either aid in elastic recoil of the lung 34 or the covering 40 may prevent the respective portion of the lung 34 from expanding during inspiration.

In the illustration of FIG. 6B, the cover 38, which is placed over the lung 34, assists in the elastic recoil of the lung allowing the lung to return to a compressed size. Assisting the lung in returning to a compressed size also helps evacuate the air from within the lung. Although the covering 38 is illustrated as encompassing the entire lung 34, it is also intended that only a portion of the lung 34 may be covered. FIG. 6B illustrates a state of the lungs immediately after exhalation. In this illustration, the lung 34 with the covering 38, is depicted as being smaller than the lung 20 without the covering. This difference in size is intended as an illustration only of a hyper-inflated lung 20 as compared to a lung 34 with a device that assists in elastic recoil.

In the illustration of FIG. 6C, the cover 40 which is placed over a portion of the lung prevents this portion from expanding during inhalation and frees space within the chest cavity to allow the remaining portion of the lung 34 to expand with air to make use of the increased volume of chest cavity for oxygen exchange. For example, as illustrated in FIG. 6C, the cover 40 is placed over a portion of the lung 34 when the lung 34 is compressed. Once the lung is permitted to re-inflate, the portion of the lung 34 which was covered stays compressed allowing the remaining portion of the lung to expand in volume to take advantage of the newly increased volume within the chest wall. FIG. 6C illustrates a state of the lungs during inhalation with the cover 40 being placed over the upper lobe. As illustrated, the upper lobe 42 remains compressed, while the remaining portions of the lung increase in volume. Preferably, the covering 40 is placed over a diseased portion of the lung 34, thereby preventing the expansion of the diseased portion which allows relative healthier portions of the lung 34 to expand with air. Selectively restricting the expansion of the lung 34 maximizes the volume within the chest cavity in which the healthier portion of the lung 34 expands. Accordingly, the lung tissue which expands is able to accommodate an otherwise greater volume of air, thus increasing the oxygen exchange function of the diseased lung.

The devices of the present invention may be constructed of continuous sheets of materials having the desired elastic characteristics or the devices may be knit or woven from a single or multiple materials. As discussed throughout the application, the materials used to construct the devices include bio-compatible materials such as silicone, urethane, or any other such material. The devices may also comprise a bio-compatible material such as polyester, polytetrafluoroethylene (PTFE), expanded PTFE, polypropylene, stainless steel, titanium, a cobalt alloy (e.g., MP35N), any other bio-compatible metal or alloy, or any combination of the above. It is intended that the devices may be constructed from a combination of the materials listed above as well.

The methods and devices according to. the present invention improve lung elastic recoil or compresses diseased lung tissue and thus improves lung efficiency for patients suffering from chronic obstructive pulmonary diseases, such as emphysema. The device improves lung efficiency in a manner which is much less invasive than conventional lung volume reduction surgery which requires the surgical removal of a portion of the lung.

Although the invention has been described for use in treating emphysema, it should be understood that the invention may also be used for treatment of other types of lung disease and injury, such as chronic bronchitis.

While the invention has been described in detail with reference to the preferred variations thereof, it will be apparent to one skilled in the art that various changes and modifications can be made and equivalents employed, without departing from the present invention.

What is claimed is:

1. An apparatus for restoring lung recoil ability in a lung, the apparatus comprising:
 a bio-compatible elastic member having an elasticity which is capable of compressing lung tissue when applied to an exterior surface of a lung and which is capable of being stretched by the lung tissue during inhalation; and at least one anchor attached to the elastic member, the anchor being adapted to affix to lung tissue with the elastic member in a stretched condition to improve the elasticity of the lung.

2. The apparatus of claim 1, wherein the anchor is configured to be inserted into lung tissue.

3. The apparatus of claim 1, wherein:

the elastic member includes a first end and a second end; and the at least one anchor includes a bio-compatible adhesive for adhering the first end and the second end of the elastic member to the lung tissue.

4. The apparatus of claim 1, wherein the elastic member includes a plurality of elastic bands.

5. The apparatus of claim 4, wherein the elastic bands are continuous loops.

6. The apparatus of claim 1, wherein the elastic member includes a patch of elastic material adhered to an exterior surface of the lung.

7. The apparatus of claim 1, wherein the elastic member includes a coil spring.

8. The apparatus of claim 1, wherein:

the elastic member includes a first end and a second end; and the at least one anchor includes a first anchor secured to the first end and a second anchor secured to the second end of the elastic member, the anchors configured to be inserted into lung tissue and attach the coil spring to the lung issue.

9. An apparatus for compressing lung tissue, the apparatus comprising:

a bio-compatible elastic member having at least a first end and a second end, the elastic member having an elasticity which is capable of compressing at least a portion of lung tissue and maintaining the lung tissue in the compressed state during inhalation; and anchors located on the first end and the second end of the elastic member and being adapted to attach the elastic member to an exterior surface of the lung tissue with the elastic member in a stretched condition.

10. The apparatus of claim 9, wherein the means for fixing includes at least one anchor configured to be inserted into lung tissue.

11. The apparatus of claim 9, wherein the means for fixing includes a bio-compatible adhesive for adhering the first end and the second end of the elastic member to the lung tissue.

12. The apparatus of claim 9, wherein the elastic member includes a patch of elastic material adhered to the exterior surface of the lung.

13. An apparatus for restoring lung recoil ability in a lung, the apparatus comprising:

a bio-compatible elastic member, the elastic member comprising a plurality of elastic bands formed as continuous loops and having an elasticity which is capable of compressing lung tissue when applied to a lung and which is capable of being stretched by the lung tissue during inhalation; and at least one anchor attached to the elastic member, the anchor being adapted to affix to lung tissue with the elastic member in a stretched condition to improve the elasticity of the lung.

* * * * *